United States Patent [19]

Bartmann et al.

[11] Patent Number: 5,262,085
[45] Date of Patent: Nov. 16, 1993

[54] TRIFLUOROMETHYLENE COMPOUNDS

[75] Inventors: Ekkehard Bartmann, Erzhausen; Eike Poetsch, Mühltal; Ulrich Finkenzeller, Plankstadt; Herbert Plach, Darmstadt, all of Fed. Rep. of Germany

[73] Assignee: Merck Patent Gesellschaft mit beschrankter Haftung, Darmstadt, Fed. Rep. of Germany

[21] Appl. No.: 732,524

[22] Filed: Jul. 19, 1991

[30] Foreign Application Priority Data

Jul. 20, 1990 [DE] Fed. Rep. of Germany ....... 4023106

[51] Int. Cl.$^5$ .................. C09K 19/30; G02F 1/13; C07D 211/72; C07C 19/08
[52] U.S. Cl. .................. 252/299.63; 252/299.61; 252/299.64; 252/299.65; 252/299.66; 359/103; 359/104; 546/303; 568/327; 560/55; 560/102; 570/128

[58] Field of Search .............. 252/299.01, 299.61, 252/299.63, 299.64, 299.65, 299.66; 359/103, 104; 546/184, 303; 560/55, 65, 102; 568/327; 570/128, 129, 144

[56] References Cited

U.S. PATENT DOCUMENTS 5,045,229  9/1991  Bartmann et al. ............. 252/299.01

Primary Examiner—Robert L. Stoll
Assistant Examiner—Shean C. Wu
Attorney, Agent, or Firm—Millen, White, Zelano, & Branigan

[57] ABSTRACT

Trifluoromethylene compounds of the formula I

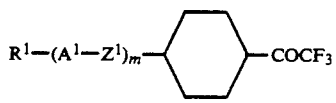

I which can be used as components of liquid-crystalline media for liquid-crystal and electrooptical display elements.

9 Claims, No Drawings

TRIFLUOROMETHYLENE COMPOUNDS

BACKGROUND OF THE INVENTION

The invention relates to trifluoromethylene compounds of the formula I

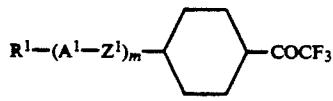

in which $R^1$ is an alkyl or alkenyl radical having 1 to 15 C atoms which is in each case unsubstituted, monosubstituted by CN or $CF_3$ or at least monosubstituted by halogen, it also being possible in these radicals for one or more $CH_2$ groups, in each case independently of one another, to be replaced by —O—,

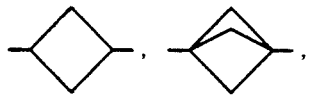

—CO—, —CO—O—, —O—CO— or —O—CO—O— in a manner such that O atoms are not linked directly to one another, $A^1$ is a (a) trans-1,4-cyclohexylene radical in which, in addition, one or more non-adjacent $CH_2$ groups may be replaced by —O— and/or —S—, (b) 1,4-phenylene radical, in which, in addition, one or two CH groups may be replaced by N, (c) radical from the group comprising 1,4-cyclohexenylene, 1,3-cyclobutylene, 1,4-bicyclo(2,2,2)octylene, piperidine-1, 4-diyl, naphthalene-2, 6-diyl, decahydronaphthalene-2,6-diyl and 1,2,3,4-tetrahydronaphthalene-2,6-diyl, where the radicals (a) and (b) may be substituted by CN or fluorine, $Z^1$ is —CO—O—, —O—CO—, —$CH_2$O—, —O$CH_2$—, —$CH_2CH_2$—, —CH=CH—, —C≡C— or a single bond and m is 1, 2 or 3.

The invention furthermore relates to the use of these compounds as components of liquid-crystalline media, and to liquid-crystal and electrooptical display elements which contain the liquid-crystalline media according to the invention.

The compounds of the formula I can be used as components of liquid-crystalline media, in particular for displays based on the principle of the twisted cell, including highly twisted variants thereof, such as, for example, supertwist nematic (STN) or supertwisted birefringence effect (SBE), the guest-host effect, the effect of deformation of aligned phases or the effect of dynamic scattering.

Similar compounds having liquid crystalline properties and one terminal $OCHF_2$ group have already been disclosed and crystal structure studies have been carried out on appropriate compounds [S. V. Sereda et al. in Kristallografiya, 32 (5), 1165 (1987) and ibid. 33 (1) 118 (1988)]. In contrast to the compounds according to the invention, however, these compounds contain nitrogen-containing bridging members. There are similar compounds having liquid-crystalline properties wherein a CO-$CF_3$ group is linked to an aromatic 1,4-phenylene group described in U.S. Pat. No. 5,045,229. However, they generally have comparatively disadvantageous values for the optic anisotropy, are not as stable against UV-irradiation and are significantly inferior to the compounds according to the invention for modern display applications.

SUMMARY OF THE INVENTION

An object of the invention is to provide stable liquid-crystalline or mesogenic compounds which are suitable as components of liquid-crystalline media and in particular have comparatively low viscosity and a moderate positive dielectric anisotropy.

Upon further study of the specification and appended claims, further objects and advantages of this invention will become apparent to those skilled in the art.

It has now been found that compounds of the formula I are preeminently suitable as components of liquid-crystalline phases. In particular, they have comparatively low viscosities. Stable liquid-crystalline phases which have a broad mesophase range, advantageous values for the optical and dielectric anisotropy and favorable values for the specific resistance can be obtained with these compounds. This gives considerable advantages, in particular in the case of media for active matrix displays or supertwist displays.

DETAILED DESCRIPTION OF THE PREFERRED EMBODIMENTS

The compounds of the formula I considerably extend the range of liquid-crystalline substances which are suitable, from various applicational points of view, for the preparation of liquid-crystalline mixtures.

The compounds of the formula I have a broad field of application. Depending on the choice of substituents, these compounds can be used as base materials from which liquid-crystalline phases are predominantly composed and they can also be added to liquid-crystalline base materials from other classes of compounds, in order, for example, to influence the dielectric and/or optical anisotropy of a dielectric of this type and/or to optimize its threshold voltage and/or its viscosity. The trifluoromethyl compounds of this invention have dielectric values of about 4.0 to 7.0 combined with optic anisotropy values of about 0.015 to 0.090. In addition, they are extraordinarily stable against UV-irradiation.

In the pure state, the compounds of the formula I are colorless and form liquid-crystalline mesophases in a very favorable temperature range for electrooptical use. They are stable chemically, thermally and to light.

The invention also relates to the compounds of the formula I, in particular compounds of the formulae I1 to I6.

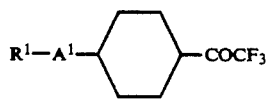

I1

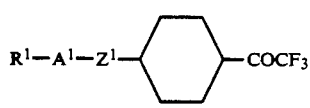

I2

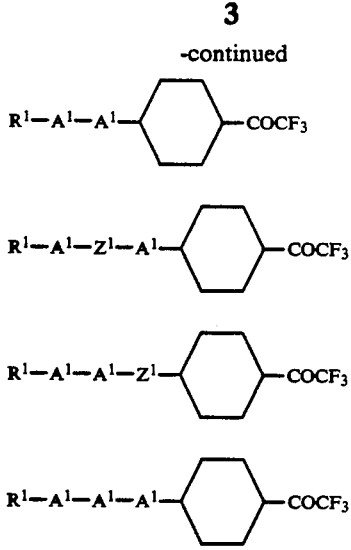

I3

I4

I5

I6

The compounds of the formula I, in which $A^1$ is a cyclohexane radical, are particularly preferred due to their high stability towards UV radiation and their low birefringence at a comparatively high anisotropy of the dielectric constants.

The invention furthermore relates to the use of these compounds as components of liquid-crystalline media. The invention furthermore relates to liquid-crystalline media containing at least one compound which contains a structural element of the formula

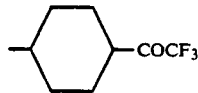

in particular a compound of the formula I, and to liquid-crystal display elements, in particular electrooptical display elements, which contain media of this type.

For simplicity, Cyc below is a 1,4-cyclohexylene radical, Che is a 1,4-cyclohexenylene radical, Dio is a 1,3-dioxane-2,5-diyl radical, Dit is a 1,3-dithiane-2,5-diyl radical, Phe is a 1,4-phenylene radical, Pyd is a pyridine-2,5-diyl radical, Pyr is a pyrimidine-2,5-diyl radical and Bi is a bicyclo(2,2,2)-octylene radical, where Cyc and/or Phe may be unsubstituted or monosubstituted or disubstituted by F or CN.

Of these, those of the sub-formulae Ia, Ib, Ic, Id, Ie, If, Ig, Ih, Ii and Il are particularly preferred.

The preferred compounds of the sub-formula Il include those of the sub-formulae Ila to Ilf:

| | |
|---|---|
| $R^1$—Phe—Cyc—COCF$_3$ | Ila |
| $R^1$—Dio—Cyc—COCF$_3$ | Ilb |
| $R^1$—Pyr—Cyc—COCF$_3$ | Ilc |
| $R^1$—Pyd—Cyc—COCF$_3$ | Ild |
| $R^1$—Cyc—Cyc—COCF$_3$ | Ile |
| $R^1$—Che—Cyc—COCF$_3$ | Ilf |

Of these, those of the formulae Ila, Ilb and Ile are particularly preferred.

The preferred compounds of the sub-formula I2 include those of the sub-formulae I2a to I2j:

| | |
|---|---|
| $R^1$—Phe—CH$_2$CH$_2$—Cyc—COCF$_3$ | I2a |
| $R^1$—Phe—OCH$_2$—Cyc—COCF$_3$ | I2b |
| $R^1$—Cyc—CH$_2$CH$_2$—Cyc—COCF$_3$ | I2c |
| $R^1$—Cyc—COO—Cyc—COCF$_3$ | I2d |
| $R^1$—A$^1$—CH$_2$CH$_2$—Cyc—COCF$_3$ | I2e |
| $R^1$—A$^1$—CH$_2$O—Cyc—COCF$_3$ | I2f |
| $R^1$A$^1$—OCH$_2$—Cyc—COCF$_3$ | I2g |
| $R^1$A$^1$—COO—Cyc—COCF$_3$ | I2h |
| $R^1$—A$^1$—OCO—Cyc—COCF$_3$ | I2i |
| $R^1$—Che—Ch$_2$CH$_2$—Cyc—COCF$_3$ | I2j |

The preferred compounds of the sub-formula I3 include those of the sub-formulae I3a to I3j:

| | |
|---|---|
| $R^1$—Phe—Phe—Cyc—CO—CF$_3$ | I3a |
| $R^1$—Phe—Dio—Cyc—CO—CF$_3$ | I3b |
| $R^1$—Cyc—Cyc—Cyc—CO—CF$_3$ | I3c |
| $R^1$—Pyd—Phe—Cyc—CO—CF$_3$ | I3d |
| $R^1$—Pyr—Phe—Cyc—CO—CF$_3$ | I3e |
| $R^1$—Phe—Pyr—Cyc—CO—CF$_3$ | I3f |
| $R^1$—Cyc—Phe—Cyc—CO—CF$_3$ | I3g |
| $R^1$—Dio—Phe—Cyc—CO—CF$_3$ | I3h |
| $R^1$—Che—Phe—Cyc—CO—CF$_3$ | I3i |
| $R^1$—Phe—Che—Cyc—CO—CF$_3$ | I3j | of these, those of the formulae I3a, I3c, I3d, I3e, I3i and I3j are particularly preferred.

The preferred compounds of the sub-formula I4 include those of the sub-formulae I4a to I4i:

| | |
|---|---|
| $R^1$—Pyr—Z$^1$—Phe—Cyc—CO—CF$_3$ | I4a |
| $R^1$—Dio—Z$^1$—Phe—Cyc—CO—CF$_3$ | I4b |
| $R^1$—Cyc—Z$^1$—Phe—Cyc—CO—CF$_3$ | I4c |
| $R^1$—Phe—Z$^1$—Cyc—Cyc—CO—CF$_3$ | I4d |
| $R^1$—Cyc—Z$^1$—Cyc—Cyc—CO—CF$_3$ | I4e |
| $R^1$—Phe—Z$^1$—Dio—Cyc—CO—CF$_3$ | I4f |
| $R^1$—Phe—Z$^1$—Phe—Cyc—CO—CF$_3$ | I4g |
| $R^1$—Phe—Z$^1$—Pyr—Cyc—CO—CF$_3$ | I4h |
| $R^1$—Phe—Z$^1$—Che—Cyc—CO—CF$_3$ | I4i |

The preferred compounds of the sub-formula I5 include those of the sub-formulae I5a to I5l:

| | |
|---|---|
| $R^1$—Pyr—Phe—Z$^1$—Cyc—COCF$_3$ | I5a |
| $R^1$—Pyr—Phe—OCH$_2$—Cyc—COCF$_3$ | I5b |

$R^1$—Phe—Phe-$Z^1$—Cyc—COCF$_3$ TM  15c $R^1$—Cyc—Cyc—$Z^1$—Cyc—COCF$_3$  15d $R^1$—Cyc—Cyc—CH$_2$CH$_2$—Cyc—COCF$_3$  15e $R^1$—Pyd—Phe—$Z^1$—Cyc—COCF$_3$  15f $R^1$—Dio—Phe—$Z^1$—Cyc—COCF$_3$  15g $R^1$—Phe—Cyc—$Z^1$—Cyc—COCF$_3$  15h $R^1$—Phe—Pyd—$Z^1$—Cyc—COCF$_3$  15i $R^1$—Che—Phe—$Z^1$—Cyc—COCF$_3$  15j $R^1$—Phe—Che—$Z^1$—Cyc—COCF$_3$  15k $R^1$—Cyc—Phe—$Z^1$—Cyc—COCF$_3$  15l

The preferred compounds of the formula II include those of the formulae 16a to 16d:

$R^1$—Phe—Phe—Phe—Cyc—COCF$_3$  16a $R^1$—Cyc—Phe—Phe—Cyc—COCF$_3$  16b $R^1$—Cyc—Cyc—Phe—Cyc—COCF$_3$  16c $R^1$—Cyc—Cyc—Cyc—Cyc—COCF$_3$  16d $R^1$ is preferably alkyl, furthermore alkoxy. $A^1$ is preferably Phe, Cyc, Che, Pyr or Dio. The compounds of the formula I preferably contain not more than one of the radicals Bi, Pyd, Pyr, Dio or Dit.

Preferred compounds of the formula I and of all the sub-formulae are those in which $A^1$ is 1,4-phenylene which is monosubstituted or disubstituted by F or monosubstituted by CN. These are, in particular, 2-fluoro-1,4-phenylene, 3-fluoro-1,4-phenylene and 2,3-difluoro-1,4-phenylene, 2,6-difluoro-1,4-phenylene and 2-cyano-1,4-phenylene and 3-cyano-1,4-phenylene.

$Z^1$ is preferably a single bond, —CO—O—, —O—CO— and —CH$_2$CH$_2$—, and secondarily preferably —CH$_2$O— and —OCH$_2$—.

If $R^1$ is an alkyl radical or an alkoxy radical, it may be straight-chain or branched. It is preferably straight-chain, has 2, 3, 4, 5, 6 or 7 C atoms and is accordingly preferably ethyl, propyl, butyl, pentyl, hexyl, heptyl, ethoxy, propoxyl butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxyll dodecoxy, tridecoxy or tetradecoxy.

Oxaalkyl is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$ is an alkenyl radical, it may be straight-chain or branched. It is preferably straight-chain and has 2 to 10 C atoms. It is accordingly particularly vinyl, prop-1- or -2-enyl, but-1-, -2- or -3-enyl, pent-1-, -2-, -3- or -4-enyl, hex-1-, -2-, -3-, 4or -5-enyl, hept-1-, -2-, -3-, -4-, -5- or -6-enyl, oct-1-, -2-, -3-, -4-, -5-, -6- or -7-enyl, non-1, -2-, -3-, -4-, -5-, -6-, -7- or -8-enyl, or dec-1-, -2-, -3-, -4-1 -5-, -6-, -7-, -8- or -9-enyl.

If $R^1$ is an alkyl radical in which one CH$_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 C atoms. They are accordingly particularly acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl and 4-(methoxycarbonyl)butyl.

If $R^1$ is an alkenyl radical in which one CH$_2$ group has been replaced by CO or CO—O or O—CO, it may be straight-chain or branched. It is preferably straight-chain and has 4 to 13 C atoms. It is accordingly particularly acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

Compounds of the formula I which contain wing groups $R^1$ which are suitable for polymerization reactions are suitable for the preparation of liquid-crystalline polymers.

Compounds of the formula I containing branched wing groups $R^1$ may occasionally be of importance due to better solubility in the customary liquid-crystalline base materials, but in particular as chiral dopes if they are optically active. Smectic compounds of this type are suitable as components of ferroelectric materials.

Compounds of the formula I having S$_A$ phases are suitable, for example, for thermally addressed displays.

Branched groups of this type generally contain not more than one chain branch. Preferred branched radicals $R^1$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-thylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 4-methylhexyl, 2-nonyl, 2-decyl, 2-dodecyl, 6-methyloctoxy, 6-methyloctaroyloxy, 5-methylheptyloxycarbonyl, 2-methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl and 2-methyl-3-oxahexyl.

If $R^1$ is an alkyl radical in which two or more CH$_2$ groups have been replaced by —O— and/or —CO—O—, it may be straight-chain or branched. It is preferably branched and has 3 to 12 C atoms. It is accordingly particularly biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl or 5,5-bis(ethoxycarbonyl)hexyl.

Compounds of the formula I which contain wing groups $R^1$ which are suitable for polycondensations are suitable for the preparation of liquid-crystalline polycondensates.

The formula I covers the racemates of these compounds and the optical antipodes, and mixtures thereof.

Of these compounds of the formula I and the subformulae, those are preferred in which at least one of the radicals present therein has one of the preferred meanings indicated.

In the compounds of the formula I, those stereoisomers in which the rings Cyc and piperidine are trans-1,4-disubstituted are preferred. Those of the abovementioned formulae which contain one or more groups Pyd, Pyr and/or Dio in each case include the two 2,5-positional isomers.

The following compounds of the formulae Ia to Ir are preferred embodiments:

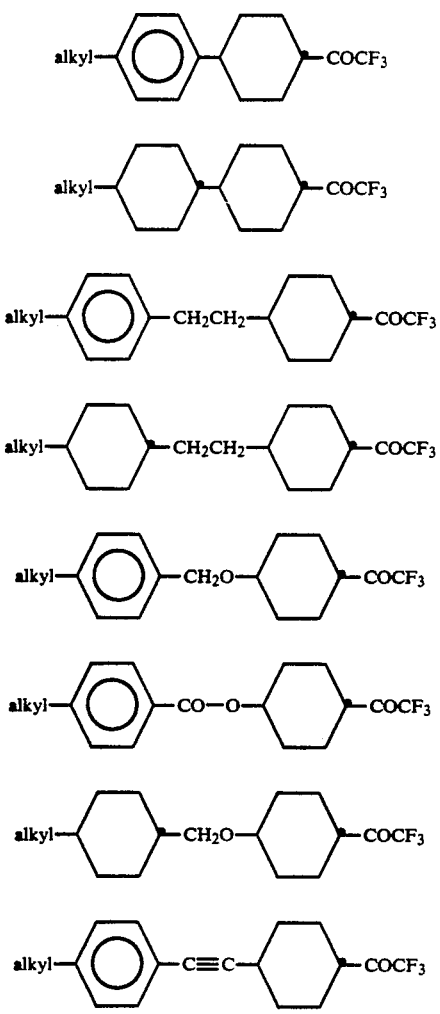

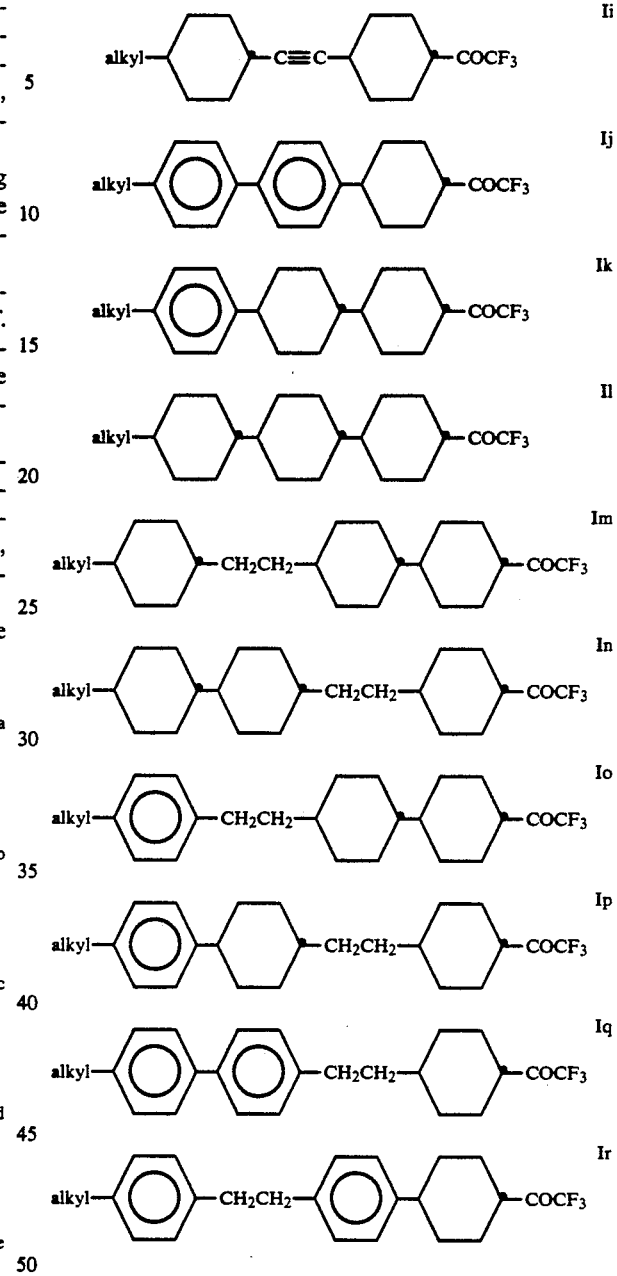

In the above compounds of the sub-formulae Ia to Ir, alkyl is alkyl or alkoxy groups having 1 to 12 C atoms, the 1,4-phenylene groups are preferably unsubstituted or substituted by one or two fluorine atoms.

The 1,4-cyclohexenylene group preferably has the following structures:

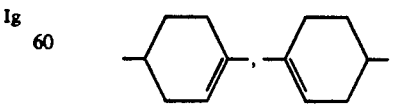

The compounds of the formula I are prepared by methods known per se, as described in the literature (for example in the standard works, such as Houben-weyl, Methoden der Organischen Chemie [Methods of organic Chemistry], Georg-Thieme-Verlag, Stuttgart, Vol. IX, pp. 867 ff.), to be precise under reaction conditions which are known and suitable for the reactions mentioned. Use can also be made here of variants which are known per se, but are not described in great detail here.

Trifluoromethyl-cyclohexyl ketones of the formula I can be, prepared, for example, in accordance with scheme I.

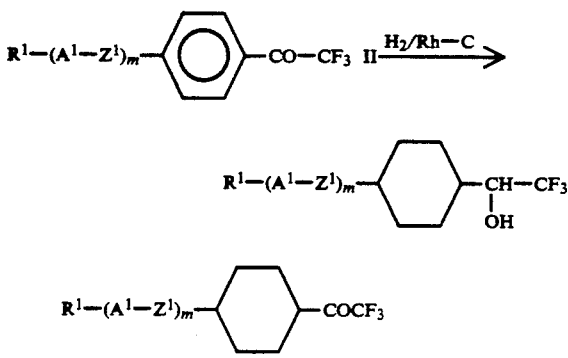

The required starting materials of the formula II can be prepared, for example, by reacting the appropriate aryl compounds with trifluoroacetyl chloride under Frieder-Crafts conditions (for example J. H. Simons et al., J. Am. Chem. Soc. 65 (1943), 389).

If desired, the starting materials can also be formed in situ by not isolating them from the reaction mixture, but instead reacting them further to form the compounds of the formula I.

Thus, the compounds of the formula I can be prepared by reducing a compound which contains one or more reducible groups and/or C—C bonds in place of H atoms, but otherwise corresponds to the formula I.

Suitable reducible groups are preferably carbonyl groups, in particular keto groups, furthermore for example, free or esterified hydroxyl groups or aromatically bound halogen atoms. Preferred starting materials for the reduction correspond to the formula I, but can contain a cyclohexene ring or cyclohexanone ring in place of a cyclohexane ring and/or can contain a —CH=CH— group in place of a —CH$_2$CH$_2$— group and/or can contain a —CO—group in place of a —CH$_2$— group and/or can contain a free or functionally (for example in the form of its p-toluenesulfonate) derived OH group in place of an H atom.

The reduction can be carried out, for example, by catalytic hydrogenation at temperatures between about 0° and about 200° and at pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are preferably noble metals, such as Pt or Pd, which can be employed in the form of oxides (for example PtO$_2$ or PdO), on a support (for example Pd on charcoal, calcium carbonate or strontium carbonate) or in finely divided form.

Ketones can also be reduced by the methods of Clemmensen (using zinc, zinc amalgam or tin and hydrochloric acid, preferably in aqueous-alcoholic solution or in the heterogeneous phase with water/toluene at temperatures between about 80° and 120°) or Wolff-Kishner (using hydrazine, preferably in the presence of alkali, such as KOH or NaOH, in a high-boiling solvent, such as diethylene glycol or triethylene glycol, at temperatures between about 100° and 200°) to form the corresponding compounds of the formula I which contain alkyl groups and/or —CH$_2$CH$_2$—bridges.

In addition, reductions using complex hydrides are possible. For example, arylsulfonyloxy groups can be removed reductively using LiAlH$_4$, in particular p-toluenesulfonyloxymethyl groups are reduced to methyl groups, preferably in an inert solvent, such as diethyl ether or THF, at temperatures of between about 0° and 100°. Double bonds can be hydrogenated using NaBH$_4$ or tributyltin hydride in methanol.

Compounds of the formula I which contain 1,4-cyclohexenylene radicals in place of 1,4-phenylene radicals but otherwise correspond to the formula I can be oxidized,, for example, using DDQ (dichlorodicyanobenzocluinone) in a suitable solvent.

Esters of the formula I can also be obtained by esterification of appropriate carboxylic acids (or reactive derivatives thereof) using alcohols or phenols (or reactive derivatives thereof) or by the DCC method (DCC=dicyclohexylcarbodiimide).

The corresponding carboxylic acids and alcohols or phenols are known or can e prepared analogously to known processes.

Suitable reactive derivatives of the carboxylic acids mentioned are, in particular, the acyl halides, above all the chlorides and bromides, furthermore the anhydrides, for example also mixed anhydrides, azides or esters, in particular alkyl esters having 1–4 C atoms in the alkyl group.

Suitable reactive derivatives of the alcohols or phenols mentioned are, in particular, the corresponding metal alkoxides or phenoxides, preferably of an alkali metal such as sodium or potassium.

The esterification is advantageously carried out in the presence of an inert solvent. Highly suitable solvents are, in particular, ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane, dichloromethane or tetrachloroethylene, and sulfoxides, such as dimethyl sulfoxide or sulfolane.

Ethers of the formula I can be obtained by etherification of corresponding hydroxyl compounds, preferably corresponding phenols, the hydroxyl compound expediently first being converted into a corresponding metal derivative, for example into the corresponding alkali metal alcoholate or alkali metal phenolate by treatment with NaH, NaNH$_2$, NaOH, KOH, Na$_2$CO, or K$_2$CO$_3$. This can then be reacted with the appropriate alkyl halide, sulfonate or dialkyl sulfate, expediently in an inert solvent, such as acetone, 1,2-dimethoxyethane, DMF or dimethyl sulfoxide, or also an excess of aqueous or aqueous-alcoholic NaOH or KOH, at temperatures between about 20° and 100°.

Compounds of the formula I in which A$^1$ is substituted by at least one F atom and/or one CN group can also be obtained from the corresponding diazonium salts by replacement of the diazonium group by a fluorine atom or by a CN group, for example by the methods of Schiemann or Sandmeyer.

Dioxane derivatives and dithiane derivatives of the formula I are expediently prepared by reacting an appropriate aldehyde (or a reactive derivative thereof) with an appropriate 1,3-diol (or a reactive derivative thereof) or an appropriate 1,3-dithiol, preferably in the presence of an inert solvent, such as benzene or toluene, and/or in the presence of a catalyst, for example a strong acid such as sulfuric acid, benzenesulfonic acid or p-toluenesulfonic acid, at temperatures between about 20° and about 150°, preferably between 80° and 120°. Suitable reactive derivatives of the starting materials are primarily acetals.

Some of the aldehydes, 1,3-diols and 1,3-dithiols mentioned, and some of the reactive derivatives thereof, are known, but they can all be prepared without difficulties from compounds known from the literature by standard methods of organic chemistry. For example, the aldehydes can be obtained by oxidation of corresponding alcohols or by reduction of nitrites or corresponding carboxylic acids or derivatives thereof, the diols can be obtained by reduction of corresponding diesters, and the dithiols can be obtained by reaction of nitriles or corresponding dihalides with NaSH.

The liquid-crystalline media according to the invention preferably contain 2 to 40, in particular 4 to 30, components as further components besides one or more compounds according to the invention. These media very particularly preferably contain 7 to 25 components besides one or more compounds according to the invention. These further components are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further components of media according to the invention can be characterized by the formulae 1, 2, 3, 4 and 5:

    R'—L—E—R"    1

    R'—L—COO—E—R"    2

    R'—L—OOC—E—R"    3

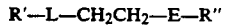    R'—L—CH$_2$CH$_2$—E—R"    4

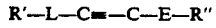    R'—L—C≡C—E—R"    5

In the formulae 1, 2, 3, 4 and 5, L and E, which may be identical or different, are in each case, independently of one another, a bivalent radical from the group formed by —Phe—, —Cyc—, —Phe—Phe, —Phe—Cyc—, —Cyc—Cyc—, —Pyr—, —Dio—, —G—Phe— and —G—Cyc— and their mirror images, where Phe is unsubstituted or fluorinesubstituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe—Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group comprising —Phe—Cyc—, —Cyc—Cyc—, —G—Phe— and —G—Cyc—.

In the compounds of the sub-formulae 1a, 2a, 3a, 4a and 5a, R' and R" are in each case, independently of one another, alkyl, alkenyl, alkoxy, alkenyloxy or alkanoyloxy having up to 8 carbon atoms. In most of these compounds, R' and R" are different from one another, one of these radicals usually being alkyl or alkenyl. In the compounds of the sub-formulae 1b, 2b, 3b, 4b and 5b, R" is —CN, —CF$_3$, —OCF$_3$, OCF$_2$H, F, Cl or —NCS; in this case, R has the meaning given for the compounds of the subformulae 1a to 5a and is preferably alkyl or alkenyl. However, other variants of the proposed substituents in the compounds of the formulae 1, 2, 3, 4 and 5 are common. Many such substances or alternatively mixtures thereof are commercially available. All these substances can be obtained by methods which are known from the literature or analogously thereto.

Besides components from the group comprising the compounds 1a, 2a, 3a, 4a and 5a (Group 1), the media according to the invention also contain components from the group comprising the compounds 1b, 2b, 3b, 4b and 5b (Group 2), whose proportions are preferably as follows: Group 1: 20 to 90%, in particular 30 to 90%, Group 2: 10 to 80%, in particular 10 to 50%, the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 40 23 106.2, are hereby incorporated by reference.

The examples below are intended to illustrate the invention without representing a limitation. mp.=melting point, cp/=clear point. "Customary work-up" means that water is added, the mixture is extracted with methylene chloride, the organic phase is separated off, dried and evaporated, the product is purified by crystallization and/or chromatography.

In addition, the abbreviations have the following meanings: C: crystalline-solid state, S: smectic phase (the index characterizes the phase type), N: nematic state, Ch: cholesteric phase, I: isotropic phase. The number between two symbols indicates the conversion temperature in degrees Celsius.

DAST:Diethylaminosulfur trifluoride
DCC:Dicyclohexylcarbodiimide
DDQ:Dichlorodicyanobenzoquinone
DIBALH:Diisobutylaluminum hydride
KOT:Potassium tertiary-butanolate
THF:Tetrahydrofuran
pTSOH:p-Toluenesulfonic acid

EXAMPLES

Example 1 trans,trans-4-Propyl-4'-(trifluoroacetyl)bicyclohexyl
1A trans,trans-4-propyl-41-(2,2,2-trifluoro-1-hydroxyethyl)bicyclohexane 16 mmol of p-(trans-4-propylcyclohexyl) trifluoroacetylbenzene (prepared in accordance with Example 4) are dissolved in 50 ml of glacial acetic acid and hydrogenated to saturation at room temperature and atmospheric pressure using 1 g of rhodium/charcoal (5%) as catalyst. The hydrogenation solution is concentrated by rotary evaporation and the residue is recrystallized twice from hexane, C 107 I.

1B A mixture of 0.12 mol of 1A, 0.18 mol of pyridinium chlorochromate and 200 ml of dichloromethane is stirred for 72 hours at room temperature. Customary work-up and chromatography give the product, C 43 I, $\Delta e=5.1$, $\Delta n=0.011$.

The following are prepared analogously

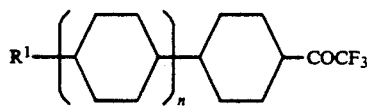

| $R^1$ | n |
|---|---|
| $C_5H_{11}$ | 0 |
| $C_7H_{11}$ | 0 |
| $C_3H_7$ | 1 |
| $C_5H_{11}$ | 1, C 103 $S_B$ 173 N 188.8 I, $\Delta\epsilon = 5.2$ $\Delta n = 0.078$ |

Mixture Example A

A liquid-crystalline medium is prepared, comprising the following components:

11% by weight of trans-1-p-propylphenyl-4-pentylcyclohexane

16% by weight of 4'-(2-(trans-4-propylcyclohexyl)ethyl)-4-ethyl-2-fluorobiphenyl 10% by weight of 4'-(2-(trans-4-propylcyclohexyl)ethyl)-4-pentyl-2-fluorobiphenyl 9% by weight of 4-ethyl-4'-(trans-4-propylcyclohexyl)-biphenyl 4% by weight of 4,41-bis(trans-4-propylcyclohexyl)-biphenyl 4% by weight of 4,41-bis(trans-4-pentylcyclohexyl)-biphenyl 4% by weight of 4-(trans-4-propylcyclohexyl)-4'-(trans-4-pentylcyclohexyl)-biphenyl 6% by weight of 4,4'-bis(trans-4-propylcyclohexyl)-2-fluorobiphenyl 6% by weight of 4,4'-bis(trans-4-pentylcyclohexyl)-2-fluorobiphenyl 30% by weight of trans,trans-4-propyl-4'-(2-trifluoroacetyl)bicyclohexyl)

This medium has a nematic phase range of above 80° C., a threshold voltage of about 3 V and an unusually high resistance in the display and is thus particularly suitable for use in active matrix displays.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A trifluoromethylene compound of the formula I

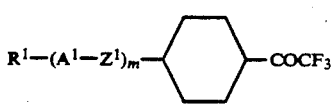

in which $R^1$ is an alkyl or alkenyl radical having 1 to 15 C atoms which is unsubstituted, monosubstituted by CN, $CF_3$ or halogen, wherein one or more $CH_2$ groups, in each case independently of one another, can be-replaced by —O—,

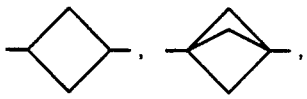,

—CO—, —CO—O—, —O—CO— or —O—CO—O— in a manner such that O atoms are not linked directly to one another, A¹ is a
(a) trans-1,4-cyclohexylene radical in which one or more non-adjacent CH₂ groups may be optionally replaced by —O— and/or —S—,
(b) 1,4-phenylene radical, in which one or two CH groups may optionally be replaced by N,
(c) radical from the group consisting of 1,4-cyclohexenylene, 1,3-cyclobutylene, 1,4-bicyclo(2,2,2)octylene, piperidine-1,4-diyl, naphthalene-2,6-diyl, decahydronaphthalene-2,6-diyl and 1,2,3,4-tetrahydronaphthalene-2,6-diyl, where the radicals (a) and (b) may be substituted by CN or fluorine, $Z^1$ is —CO—O—, —O—CO—, —CH₂—, OCH₂—, —CH₂CH₂—, —CH=CH—, —C≡C— or a single bond and m is 1, 2 or 3.

2. A trifluoromethylene compound according to claim 1, characterized by the formula I1

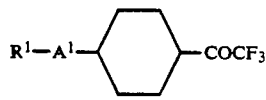 I1 in which R¹ and A¹ are as defined in claim 1.

3. A trifluoromethylene compound according to claim 1, characterized by the formula I2

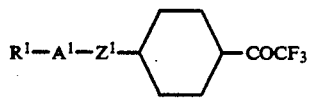 I2 in which R¹, Z¹ and A¹ are as defined in claim 1.

4. A trifluoromethylene compound according to claim 1, characterized by the formula I3

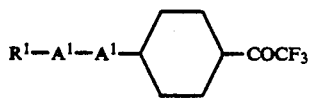 I3 in which R¹ and A¹ are as defined in claim 1.

5. A trifluoromethylene compound according to claim 1, characterized in that A¹, in each case independently of one another, is trans-1,4-cyclohexylene or 1,4-phenylene.

6. A trifluoromethylene compound according to claim 1, wherein Z¹, in each case independently of one another, is —CH₂CH₂—, —C≡C— or a single bond.

7. A liquid-crystalline medium comprising at least two liquid-crystalline compounds, wherein at least one compound is of the formula I of claim 1.

8. A liquid-crystal display element that contains a liquid-crystalline medium according to claim 7.

9. An electrooptical display element that contains, as dielectric, a liquid-crystalline medium according to claim 8.

* * * * *